United States Patent [19]

Tung et al.

[11] Patent Number: 5,763,706

[45] Date of Patent: Jun. 9, 1998

[54] PROCESS FOR THE MANUFACTURE OF 1,1, 1,3,3-PENTAFLUOROPROPANE AND 1,1,1,3,3, 3-HEXAFLUOROPROPANE

[75] Inventors: Hsueh Sung Tung, Getzville; Daniel Chistopher Merkel, West Seneca, both of N.Y.; Zenart Joseph Dziadyk, Lancaster, Canada; Clayton Herbert Carson, Clarence Center; Hang Thanh Pham, Amherst, both of N.Y.

[73] Assignee: AlliedSignal Inc., Morristown, N.J.

[21] Appl. No.: 675,020

[22] Filed: Jul. 3, 1996

[51] Int. Cl.⁶ ................................................. C07C 17/08
[52] U.S. Cl. ................................................. 570/167
[58] Field of Search ........................................ 570/167

[56] References Cited

U.S. PATENT DOCUMENTS 5,574,192  11/1996  VanDerPuy et al. .................. 570/167
5,616,819  4/1997   Boyce et al. ......................... 570/167
5,659,093  8/1997   Takubo et al. ....................... 570/167

FOREIGN PATENT DOCUMENTS 684687       4/1964   Canada.
WO 95/04022  2/1995   WIPO.

*Primary Examiner*—Paul F. Shaver
*Attorney, Agent, or Firm*—Jay P. Friedenson

[57] ABSTRACT

An integrated manufacturing process for producing HFC-245fa, HFC-236fa or a mixture thereof by reaction of HCC-240fa, HCC-230 or a mixture thereof with HF. HCC-240fa, HCC-230 or a mixture thereof is reacted with hydrogen fluoride in a liquid phase in the presence of a fluorination catalyst. Optionally, produced HCl is removed by distillation. HF present is thereafter recovered by liquid-vapor extraction. Unsaturated compounds are then removed by photochlorination and HFC-245fa, HFC-236fa or a mixture thereof is obtained by distillation.

27 Claims, 1 Drawing Sheet

PROCESS FOR THE MANUFACTURE OF 1,1,1,3,3-PENTAFLUOROPROPANE AND 1,1,1,3,3,3-HEXAFLUOROPROPANE

BACKGROUND OF THE INVENTION

1. Field of the Invention

The present invention relates to the preparation of hydrofluorocarbons. More particularly, the invention pertains to a method for the preparation of 1,1,1,3,3-pentafluoropropane (HFC-245fa) and 1,1,1,3,3,3-hexafluoropropane (HFC-236fa) or a mixture thereof. Specifically, the invention concerns an integrated manufacturing process for producing HFC-245fa, HFC-236fa or a mixture thereof by the reaction of 1,1,1,3,3-pentachloropropane (HCC-240fa), 1,1,1,3,3,3-hexachloropropane (HCC-230) or a mixture thereof with hydrogen fluoride.

2. Description of the Prior Art

Recently, there has been widespread concern that chlorofluorocarbons might be detrimental to the Earth's ozone layer. As a result, there is a worldwide effort to use halocarbons which contain fewer chlorine substituents. In this regard, 1,1,1,3,3-pentafluoropropane and 1,1,1,3,3,3-hexafluoropropane are hydrofluorocarbons having zero ozone depletion potential, and are being considered as replacements for chlorofluorocarbons in foams, refrigeration and other systems. The production of hydrofluorocarbons, i.e. compounds containing only carbon, hydrogen and fluorine has been the subject of interest to provide environmentally desirable products for use as solvents, foam blowing agents, refrigerants, cleaning agents, aerosol propellants, heat transfer media, dielectrics, fire extinguishing compositions and power cycle working fluids. It is known in the art to produce hydrofluorocarbons (HFCs) by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are non-ozone depleting, but also is they are also non-flammable and non-toxic as compared to the chlorine containing compounds. HFC-245fa itself is well known in the art as described in U.S. Pat. No. 2,942,036, Canadian 684,687, EP 381 986A, JP 02.272,086 and WO 95/04022. HFC-236fa is known from U.S. Pat. No. 5,395,997. All of the foregoing patents are incorporated herein by reference. However, it has been a problem in the art to conduct an economical process for the continuous preparation of HFC-245fa and HFC-236fa. It has now been found that HFC-245fa or HFC-236fa may be continuously and economically produced in an integrated manufacturing process by the reaction of HCC-240fa or HCC-230 with hydrogen fluoride. The HCC-240fa, HCC-230 or mixtures thereof and HF are first reacted in a liquid phase catalytic reaction, HCl is then optionally removed by distillation, HF is recovered, preferably by liquid-vapor or liquid—liquid extraction and then optionally recycled. Unsaturates are thereafter removed by photochlorination and HFC-245fa, HFC-236fa or a mixture thereof is obtained by distillation.

SUMMARY OF THE INVENTION

The invention provides a process for the preparation of fluoropropanes which comprises (a) reacting a compound selected from the group consisting of 1,1,1,3,3-pentachloropropane; 1,1,1,3,3,3-hexachloropropane and mixtures thereof with hydrogen fluoride in the presence of a fluorination catalyst;

(b) optionally removing HCl produced by step (a); and (c) recovering HF present after step (b).

Preferably the process comprises the subsequent further steps of (d) removing unsaturated compounds present after step (c) by photochlorination; and (e) recovering 1,1,1,3,3-pentafluoropropane; 1,1,1,3,3,3-hexafluoropropane or a mixture thereof from the result of step (d) by distillation.

The invention also comprises a process for the preparation of fluoropropanes which comprises (a) reacting a compound selected from the group consisting of 1,1,1,3,3-pentachloropropane; 1,1,1,3,3,3-hexachloropropane and mixtures thereof with hydrogen fluoride in a liquid phase in the presence of a fluorination catalyst;

(b) optionally removing HCl produced by step (a) by distillation; and (c) recovering HF present after step (b) by liquid-vapor or liquid—liquid extraction;

(d) optionally removing unsaturated compounds present after step (c) by photochlorination; and (e) recovering 1,1,1,3,3-pentafluoropropane; 1,1,1,3,3,3-hexafluoropropane or a mixture thereof from the result of step (d) by distillation.

DETAILED DESCRIPTION OF THE PREFERRED EMBODIMENT

Figure 1:
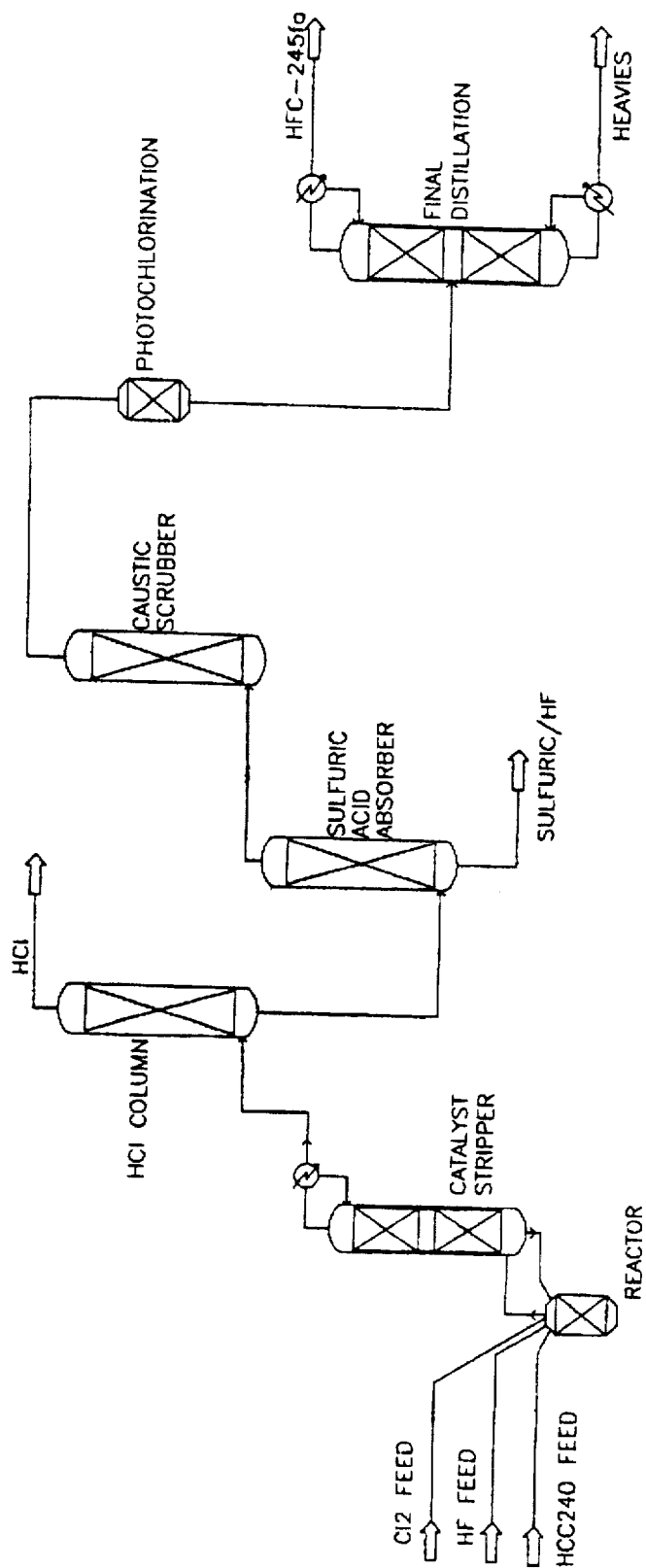
FIG. 1 shows a schematic view of a reaction sequence according to the present invention.

In the practice of the present invention, a fluorination catalyst, preferably a liquid phase catalyst is charged to a fluorination reactor prior to heating of the reactor. Useful fluorination catalysts non-exclusively include transition metal halides, Group IVb metal halides and Group Vb metal halides and mixtures thereof. Such non-exclusively include chrome halides, $SbCl_5$, $SbCl_3$, $TaCl_5$, $SnCl_4$, $NbCl_5$, $TiCl_4$, $MoCl_5$ and mixtures thereof. The reactor according to this invention may be any suitable fluorination reaction vessel but it should be constructed from materials which are resistant to the corrosive effects of hydrogen fluoride such as Hastalloy, Inconel, Monel and fluoropolymer-lined vessels. FIG. 1 shows the reaction of HF and HCC-240fa in the production of HFC-245fa, however alternatively, HCC-230 would be substituted for HCC-240 in the production of HFC-236fa or a mixture of HCC-230 and HCC-240 substituted to form a mixture of HFC-245fa and HFC 236fa. As seen in FIG. 1, HCC-240 and HF are simultaneously fed to the reactor. This is done after the reactor reaches the desired temperature. The reactor is run at a preferred temperature ranging from about 60° to about 140° C.; more preferably from about 70° to about 120° C. and most preferably from about 80° to about 110° C. The HF to HCC-240fa or HCC-230 mole ratio preferably ranges from about 4 to about 10; more preferably from about 5 to about 9 and most preferably from about 5.5 to about 8. Reactor pressure is preferably maintained at from about 50 to about 300 psig; more preferably from about 100 to about 275 psig and most preferably from about 125 to about 260 psig. A chlorine feed is optional, but preferred to keep the catalyst active. A chlorine feed is especially advantageous when antimony chloride is used as catalyst. For every pound of $SbCl_5$ catalyst, about 0.06 to about 0.2 lb. of chlorine is fed to the reactor. Chlorine can be charged in either a batch or continuous mode.

Optionally, but preferably, a top catalyst stripper is used such that most of the unreacted HF and catalyst is refluxed back to the reactor. The catalyst stripper is a packed pipe equipped with a condenser and this step is conducted by adjusting the temperature of the condenser to a range of from about 20° C. to about 100° C.

The effluent from the catalyst stripper is then optionally, but preferably, fed to an HCl distillation column to remove relatively pure HCl from the reaction mixture exiting the catalyst stripper. The pressure of the HCl column is preferred to match that of the reactor.

The essentially HCl free organic/HF mixture exiting the HCl column is optionally fed to a distillation column (not shown in FIG. 1) to remove heavy reaction products before the resulting mixture enters a sulfuric acid absorber. The pressure of this column is preferably maintained at from about 200 psig or less, more preferably from about 150 psig or less and most preferably from about 100 psig or less. The overhead of the distillation column contains HHFC-245fa or HFC-236fa, volatile by-products as impurities and unreacted HF. The bottom cuts of the distillation column contains recyclable and non-recyclable heavies. The recyclable heavies are recycled back to the step (a) reactor. The non-recyclable heavies are disposed of.

The process then performs a step (c) of recovering HF present after step (b). This is preferably conducted by vapor-liquid or liquid—liquid extraction. This is preferably performed with a sulfuric acid absorber followed by a caustic or water scrubber. The mixture of fluorocarbons resulting from step (b) is in admixture with hydrogen fluoride. The HFC and HF may be separated by adding sulfuric acid to the HFC/HF mixture. This forms a phase rich in HFC and phase rich in the hydrogen fluoride and sulfuric acid. Sulfuric acid is preferably added such that the weight ratio of sulfuric acid to hydrogen fluoride ranges from about 1:1 to about 10:1. More preferably the weight ratio ranges from about 1:1 to about 8:1 and most preferably from about 2:1 to about 4:1. Preferably the extraction is conducted at a temperature of from about −20° C. to about 100° C., more preferably from about −10° C. to about 60° C., and most preferably from about 0° C. to about 40° C. The reaction is usually conducted at normal atmospheric pressure, however, higher or lower pressure conditions may be used by those skilled in the art. Pressure is preferably about 100 psig or less; more preferably about 50 psig or less, and most preferably about 20 psig or less.

The sulfuric acid/HF mixture from the sulfuric acid absorber is fed to a HF recovery column (not shown in FIG. 1). The HF and sulfuric acid may then be recycled. That is, the BF may be recirculated to the step (a) starting reaction for the formation of the HFC-245fa or HFC-236fa and the sulfuric acid may be recycled for use in the extraction step(c). The organic portion of the mixture exiting the sulfuric acid absorber is optionally fed into a distillation column (not shown in FIG. 1) to remove light products which are recycled.

Upon adding the sulfuric acid to the mixture of fluorocarbon and HF, two phases form. An upper phase is formed which is rich in organics and a lower phase which is rich in HF/sulfuric acid. By the term "rich" is meant, the phase contains more than 50% of the indicated component in that phase, and preferably more than 80% of the indicated component in that phase. The extraction efficiency of the fluorocarbon can range from about 90% to about 99%. After the separation of the phases, one removes the upper phase rich in the organics from the lower phase rich in the hydrogen fluoride and sulfuric acid. One may optionally repeat the extraction by adding more sulfuric acid. Preferably one thereafter separates the hydrogen fluoride and sulfuric acid from the removed lower phase.

Alternatively the sulfuric acid absorber may be replaced by a HF/water azeotrope absorber. The HF/water azeotrope weight ratio is preferably maintained at about 42% HF and 58% water. HF is extracted and recycled back to the reactor in the same manner as in the sulfuric acid.

The HFC-245fa or HFC-236fa rich stream exiting either the light column or the sulfuric acid absorber is fed to a caustic or water scrubber for removal of acidity. Such a scrubber is well known in the art and conventionally comprises a caustic scrubbing with aqueous NaOH or KOH under conditions sufficient to neutralize residual acidity.

A photochlorination unit is then used to remove unsaturates in the HFC-245fa or HFC-236fa stream. This is done by adding chlorine to the stream to react with unsaturates in the presence of UV light. Photochlorination of unsaturates is itself well known in the art. The mole ratio of $Cl_2$/total unsaturates is preferably about 5 or less, more preferably about 4 or less, and most preferably about 3 or less. Pressure is not critical, although it is preferably operated under atmospheric or subatmospheric pressure. Temperature is preferably about 60° C. or less, more preferably about 40° C. or less and most preferably about 15° C. or less. UV light preferably has a wavelength of less than about 400 nanometers. The mixture is exposed to the UV light for a time and at an energy level sufficient to reduce unsaturates to less than about 500 ppm.

HFC-245fa or HFC-236fa is then recovered in a step (e) by distillation of the intermediate resulting from step (d). Distillation can be a batch or continuous distillation. In the batch mode, one distillation column is sufficient. In a continuous mode, two distillation columns may be required, one to remove light distillates and the other to remove heavies. Pressure of the distillation(s) is preferred to run at about 200 psig or less, more preferably about 150 psig or less and most preferably about 100 psig or less.

The HFC-245fa or HFC-236fa produced has a purity of at least about 99.5%. The reactions of the present invention may be conducted in either a batch or continuous mode of operation, however, continuous operation is preferred.

The following non-limiting examples serve to illustrate the invention.

EXAMPLE 1

400 lbs. of antimony pentachloride catalyst is charged into a 50 gallon reactor. The reactor temperature is raised to 95° C. 605 lbs./day of HCC-240, 332 lbs./day of HF and 36 lbs./day of chlorine are fed to the reactor continuously. The reactor pressure is maintained at about 150 psig. The product stream contains HFC-245fa, HF, HCl and organic by-products including 1,3,3,3-tetrafluoropropene, 1-chloro-3,3,3-trifluoropropene, and 1-chloro-1,3,3,3-tetrafluoropropene. About 504 lbs./day of HCl is removed from the product stream by low temperature distillation. The HCl free product stream is then fed to a sulfuric acid absorber to extract excess HF and to recycle HF back to the reactor. The effluent of the absorber is fed to a acid scrubber to remove trace amounts of HF. The HF-free product stream is then fed to a photochlorinator. Chlorine is added to remove the unsaturates in the presence of UV light. The excess chlorine is removed by aqueous wash by using caustic and sodium sulfite. The chlorine-free effluent is then dried and fed to a final distillation. The HFC-245fa produced has high quality (99.5% purity) and about 300 lbs./day is produced. The single pass yield is about 80%. The yield with recycle of heavies and lights is greater than 90%.

EXAMPLE 2

Example 1 is repeated except a distillation column is added after the HCl column and before the sulfuric acid absorber. This column is used to remove the heavies from the crude product stream exiting the HCl column. About 50% of the heavies are recyclable and are recycled back to the reactor. The light product mixture exiting the top of the heavies column is fed back to the sulfuric acid absorber. The HFC-245fa produced is greater than 300 lbs./day.

EXAMPLE 3

Example 2 is repeated except an additional distillation column is added between the caustic scrubber and the sulfuric acid absorber to remove and recycle light intermediates. The bottoms of this distillation column is fed to the caustic scrubber. The HFC-245fa produced is greater than 300 lbs./day.

EXAMPLE 4

Example 1 is repeated except a distillation column is added before the photochlorinator and after the caustic scrubber to remove and recycle the light by-products. The bottom of this lights distillation column is fed to the photochlorinator. The HFC-245fa produced is greater than 300 lbs./day.

EXAMPLE 5

Example 1 is repeated except the sulfuric acid absorber is replaced by HF/water azeotrope absorber. The BF/water azeotrope weight ratio is maintained at about 42% HF and 58% water. HF is extracted and recycled back to the reactor in the same manner as in the sulfuric acid.

EXAMPLE 6

A 2.5 gallon PTFE-lined reactor is charged with 5 lbs. HF and 1.2 lbs. antimony pentachloride catalyst. 6.2 lbs. of 1,1,1,3,3,3-hexachloropropane are charged into the reactor. The reactor temperature is brought to 92° C. and pressure is controlled at less than 240 psig. Hourly samples are taken during the batch run. After 7 hours the reaction is complete and the yield of HFC-236fa is approximately 88%.

EXAMPLE 7

Example 1 is repeated except the organic feed is changed from HCC-240 (1,1,1,3,3-pentachloropropane) to HCC-230 (1,1,1,3,3,3-hexachloropropane). The reaction is conducted at 95° C. The yield of HFC-236fa is 90%.

What is claimed is:

1. A process for the preparation of fluoropropanes which comprises (a) reacting a compound selected from the group consisting of 1,1,1,3,3-pentachloropropane; 1,1,1,3,3,3-hexachloropropane and mixtures thereof with hydrogen fluoride in the presence of a fluorination catalyst;

(b) optionally removing HCl produced by step (a); and (c) recovering HF present after step (b).

2. The process of claim 1 further comprising the subsequent steps of: (d) removing unsaturated compounds present after step (c) by photochlorination; and (e) recovering 1,1,1,3,3-pentafluoropropane; 1,1,1,3,3,3-hexafluoropropane or a mixture thereof from the result of step (d) by distillation.

3. The process of claim 1 wherein step (a) is conducted in a liquid phase.

4. The process of claim 1 wherein the fluorination catalyst is selected from the group consisting of transition metal halides. Group IVb metal halides and Group Vb metal halides and mixtures thereof.

5. The process of claim 1 wherein the fluorination catalyst is selected from the group consisting of chrome halides. $SbCl_5$, $SbCl_3$, $TaCl_5$, $SnCl_4$, $NbCl_5$, $TiCl_4$, $MoCl_5$ and mixtures thereof.

6. The process of claim 1 wherein step (a) is conducted at a temperature of from about 60° to about 140° C.

7. The process of claim 1 wherein step (a) is conducted at a pressure of from about 50 to about 300 psig.

8. The process of claim 1 wherein chlorine feed to reaction step (a) in an amount sufficient to maintain the catalytic activity of the catalyst.

9. The process of claim 1 wherein the HF to HCC-240fa mole ratio ranges from about 4 to about 10.

10. The process of claim 1 further comprising an additional step after step (a) and before step (b), wherein any unreacted hydrogen fluoride and catalyst in the reaction product resulting from step (a) is removed and recycled to the step (a) reaction.

11. The process of claim 1 wherein step (b) is conducted by distillation.

12. The process of claim 1 further comprising an additional step after step (b) and before step (c), comprising distilling the product resulting from step (b) to produce an overhead of the distillation column comprising 1,1,1,3,3-pentafluoropropane; 1,1,1,3,3,3-hexafluoropropane or a mixture thereof, hydrogen fluoride, unsaturated compounds and other impurities.

13. The process of claim 11 wherein the additional distilling step after step (b) and before step (c) is conducted at a pressure of from about 200 psig or less.

14. The process of claim 1 wherein step (c) is conducted by liquid-vapor extraction.

15. The process of claim 13 wherein step (c) is conducted by adding sulfuric acid to the product resulting after step (b) and then separating therefrom a mixture of sulfuric acid and HF from a reaction mass balance comprising 1,1,1,3,3-pentafluoropropane; 1,1,1,3,3,3-hexafluoropropane or a mixture thereof, unsaturated compounds and other impurities.

16. The process of claim 15 comprising the step of removing residual acids from said reaction mass balance after step (c).

17. The process of claim 16 wherein the step of removing residual acids from said reaction mass balance after step (c) is conducted with a caustic scrubber or a water scrubber.

18. The process of claim 15 further comprising separating sulfuric acid and HF from the mixture of sulfuric acid and HF.

19. The process of claim 18 further comprising recycling HF recovered from step (c) back to step (a).

20. The process of claim 2 wherein step (d) is conducted with chlorine in a mole ratio of $Cl_2$ to total unsaturated compounds is about 5 or less.

21. The process of claim 2 wherein the step (e) distillation is conducted at about 200 psig or less.

22. The process of claim 1 wherein 1,1,1,3,3-pentafluoropropane produced.

23. The process of claim 1 wherein 1,1,1,3,3,3-hexafluoropropane produced.

24. The process of claim 1 wherein a mixture of 1,1,1,3,3-pentafluoropropane and 1,1,1,3,3,3-hexafluoropropane is produced.

25. The process of claim 1 wherein steps (a) through (c) are conducted in a continuous mode.

26. The process of claim 2 wherein steps (a) through (e) are conducted in a continuous mode.

27. A process for the preparation of fluoropropanes which comprises (a) reacting a compound selected from the group consisting of 1,1,1,3,3-pentachloropropane; 1,1,1,3,3,3-hexachloropropane and mixtures thereof with hydrogen fluoride in a liquid phase in the presence of a fluorination catalyst;

(b) optionally removing HCl produced by step (a) by distillation; and (c) recovering HF present after step (b) by liquid-vapor or liquid—liquid extraction;

(d) optionally removing unsaturated compounds present after step (c) by photochlorination; and (e) recovering 1,1,1,3,3-pentafluoropropane; 1,1,1,3,3,3-hexafluoropropane or mixtures thereof from the result of step (d) by distillation.

* * * * *

UNITED STATES PATENT AND TRADEMARK OFFICE
CERTIFICATE OF CORRECTION

PATENT NO : 5,763,706
DATED : June 9, 1998
INVENTOR(S) : Tung et al.

It is certified that error appears in the above-identified patent and that said Letters Patent is hereby corrected as shown below:

Column 1, line 39, delete "is".

Column 3, line 19, delete "HIFC-245fa" and substitute therefor -- HFC-245fa --.

Column 3, line 50, delete "BF" and substitute therefor -- HF --.

Column 3, line 65, delete "$^{99}$%" and substitute therefor -- 99% --.

Column 5, line 35, delete "BF/water" and substitute therefor -- HF/water --.

Signed and Sealed this

Eighth Day of February, 2000

*Attest:*

*Attesting Officer*

Q. TODD DICKINSON

*Commissioner of Patents and Trademarks*